US00PP35617P2

(12) United States Plant Patent
Preesman

(10) Patent No.: US PP35,617 P2
(45) Date of Patent: Jan. 30, 2024

(54) ***PRIMULINA* PLANT NAMED 'PREESMANPT2'**

(50) Latin Name: *Primulina dryas*
Varietal Denomination: PREESMANPT2

(71) Applicant: Preesman B. V., Strijen (NL)

(72) Inventor: Kees Preesman, Strijen (NL)

(73) Assignee: Preesman B. V., Strijen (NL)

( * ) Notice: Subject to any disclaimer, the term of this patent is extended or adjusted under 35 U.S.C. 154(b) by 0 days.

(21) Appl. No.: 18/445,429

(22) Filed: Aug. 8, 2023

(51) Int. Cl.
*A01H 5/02* (2018.01)
*A01H 6/44* (2018.01)

(52) U.S. Cl.
USPC ..... Plt./263.1
CPC ..... *A01H 6/44* (2018.05)

(58) Field of Classification Search
USPC ..... Plt./263.1
CPC ..... A01H 6/44; A01H 5/02
See application file for complete search history.

*Primary Examiner* — Keith O. Robinson
(74) *Attorney, Agent, or Firm* — Samuel R. McCoy, Jr.

(57) ABSTRACT

'PREESMANPT2' is a distinctive *Primulina* plant which is characterized by a moderately fast rate of growth, broad ovate foliage that is moderately to strongly concave with coarsely crenulate leaf margins, dark green and glossy foliage that is overlaid with a light greyed-green reticulate pattern, as well as the uniformity and stability of these characteristics from generation to generation.

2 Drawing Sheets

Latin name of the genus and species: The Latin name of the genus and species of the novel variety disclosed herein is *Primulina dryas* (Dunn) Mich. Möller & A. Weber.

Variety denomination: The inventive variety of *Primulina* disclosed herein has been given the variety denomination 'PREESMANPT2'.

BACKGROUND OF THE INVENTION

Parentage: 'PREESMANPT2' originated as a naturally occurring, spontaneous, whole-plant mutation which was discovered growing amongst a cultivated population of *Primulina dryas* 'Preesman PT' plants (Dutch Plant Breeders' Rights grant number 44601). The inventor regularly discovers mutations of *Primulina dryas* at his commercial greenhouse in Strijen, the Netherlands and, as a result, a selection program was established with the goal of developing a new cultivar with novel foliage colors and patterns. In 2019, a plurality of whole-plant mutations exhibiting unique foliage coloration were discovered and subsequently isolated for further observation. Each mutation was asexually propagated by leaf cuttings and grown to maturity, in order to confirm the uniqueness and stability of the characteristics first observed. In December of 2019, 'PREESMANPT2' was ultimately selected for its combination of a unique foliage color pattern, moderately fast rate of growth, and high plant vigor.

Asexual Reproduction: Asexual reproduction of the new cultivar 'PREESMANPT2' was first performed by way of leaf cutting propagation in 2019 at the inventor's commercial greenhouse facility in Strijen, the Netherlands and later, in March of 2020, by way of meristematic tissue culture micropropagation. Through eight subsequent generations, the unique features of this cultivar have proven to be stable and true to type.

SUMMARY OF THE INVENTION

The cultivar 'PREESMANPT2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PREESMANPT2'. These characteristics in combination distinguish 'PREESMANPT2' as a new and distinct *Primulina* cultivar:

1. *Primulina* 'PREESMANPT2' exhibits a moderately fast rate of growth; and
2. *Primulina* 'PREESMANPT2' exhibits broad ovate foliage that is moderately to strongly concave with coarsely crenulate leaf margins.
3. *Primulina* 'PREESMANPT2' exhibits dark green, glossy foliage that is overlaid with a light greyed-green reticulate pattern.

BOTANICAL DESCRIPTION OF THE PLANT

Figure 1:
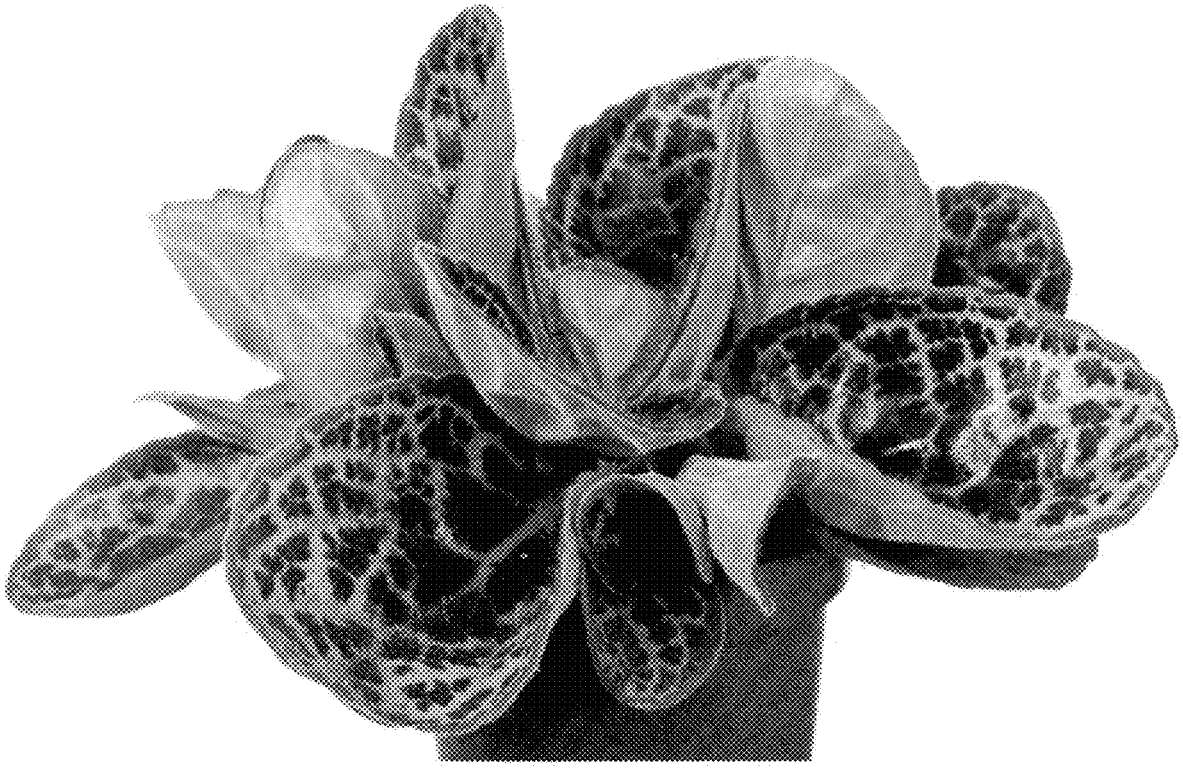
FIG. 1 illustrates, as nearly true as it is reasonably possible to make the same in color photographs of this type, an exemplary plant of 'PREESMANPT2' grown in a commercial greenhouse in Strijen, the Netherlands. This plant is approximately 15 weeks old, in a 13 cm container.
Figure 2:
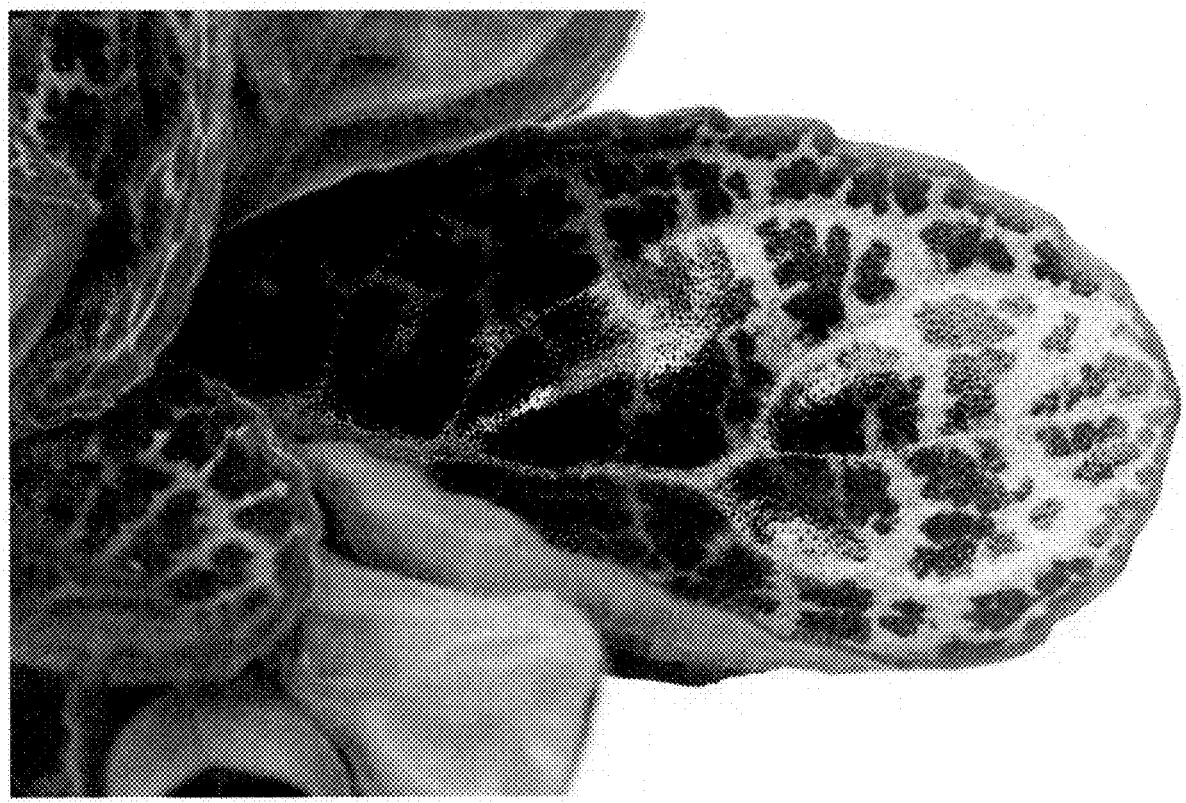
FIG. 2 illustrates, as nearly true as it is reasonably possible to make the same in color photographs of this type, the adaxial surface of the mature foliage of 'PREESMANPT2'.

The following observations and measurements, made in June of 2022, describe averages from a sample set of six 15-week-old 'PREESMANPT2' plants grown in 13 cm nursery containers, from rooted cuttings, at a greenhouse in Strijen, the Netherlands. Plants were produced using conventional greenhouse production protocols for *Primulina* sp. which consisted of growing plants under shade with light levels of 300 watts per square meter, watering with ebb and flood benches, fertigating using an A-B fertilization scheme, and employing chemical pest measures for thrips control. No photoperiodic treatments were utilized in production.

Those skilled in the art will appreciate that certain characteristics will vary with older or, conversely, with younger plants. 'PREESMANPT2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'PREESMANPT2' and a comparison with the parent plant and most similar commercial cultivar are provided below.

Plant description:

*Growth habit.*—Broad spreading to spreading-upright herbaceous perennial with foliage growing from basal shoots.

*Plant shape.*—Flattened to flattened globular.

*Height from soil level to top of foliar plane.*—14.6 cm.

*Plant spread.*—79.0 cm.

*Number of basal shoots per plant.*—8, with one primary shoot and 7 lateral shoots.

*Growth rate.*—Moderately fast-growing.

*Plant vigor.*—Highly vigorous.

*Propagation.*—Type — Asexual propagation is accomplished by way of meristematic tissue culture micropropagation. Time to initiate rooting — Approximately 140 days at 18 degrees Celsius. Time to produce a rooted cutting — Approximately 22 weeks are needed to produce a marketable plant in a 13 cm nursery container.

*Disease and pest resistance or susceptibility.*—Neither susceptibility nor resistance to pests and diseases common to *Primulina dryas* have been observed.

*Environmental tolerances.*—Adapt to temperatures as low as 5 degrees Celsius and at least as high as 40 degrees Celsius; moderate tolerance to rain; low to moderate tolerance to wind.

Roots:

*General.*—Moderately dense, moderately branched rooting; roots are fleshy and non-fibrous.

*Distribution in the soil profile.*—Shallow to moderately deep.

*Texture.*—Smooth, with fine lateral roots.

Foliage:

*Quantity.*—13 leaves along the main shoot and 5 per lateral shoot, on average.

*Arrangement.*—Alternate.

*Attachment.*—Petiolate.

*Division.*—Simple.

*Lamina.*—Shape — Broad ovate. Length — 13.3 cm, excluding the petiole. Width — 11.5 cm. Apex — Broad bluntly acute. Base — Truncate. Aspect — Moderately to strongly concave and furrowed. Margins — Coarsely crenate margins with no undulation. Luster, adaxial surface — Glossy. Luster, abaxial surface — Very slightly glossy. Texture, adaxial surface — Moderately to densely pubescent with strigose hairs with an average length of 0.4 cm and colored white, nearest to RHS NN155D. Texture, abaxial surface — Densely pubescent with soft, short hairs with an average length of 0.15 cm and colored white, nearest to RHS NN155D. Color — Juvenile foliage, adaxial surface — Green, nearest to a mixture of RHS NN137A and 139A, and fading to yellow-green towards the base, nearest to RHS 144A; veins and portions of the lamina adjacent to veins colored greyed-green, nearest to in between RHS 194A and 194B. Juvenile foliage, abaxial surface — Yellow-green, nearest to RHS 148C. Mature foliage, adaxial surface — Nearest to a mixture of yellow-green and greyed-green, RHS 147A and N189A yet considerably darker; veins and portions of the lamina adjacent to veins colored greyed-green, nearest to in between RHS 194A and 194B. Mature foliage, abaxial surface — Yellow-green, nearest to RHS N148B.

*Venation.*—Pattern — Reticulate. Color, adaxial surfaces — Greyed-green, nearest to RHS 194A. Color, abaxial surface — Yellow-green, nearest to RHS 144A.

Petiole:

*Attitude.*—Upright and outward.

*Strength.*—Moderately strong.

*Aspect.*—Flattened.

*Length.*—3.1 cm.

*Width.*—1.3 cm.

*Height.*—0.6 cm.

*Luster, adaxial surface.*—Moderately glossy.

*Luster, abaxial surface.*—Matte.

*Texture, adaxial surface.*—Moderately to densely pubescent with strigose hairs with an average length of 0.25 cm and colored white, nearest to RHS NN155D.

*Texture, abaxial surface.*—Densely pubescent with soft, short hairs with an average length of 0.15 cm and colored white, nearest to RHS NN155D.

*Color, adaxial surface.*—Yellow-green, nearest to RHS 144A, and transitioning to green towards the margins, nearest to RHS 137A.

*Color, abaxial surface.*—Yellow-green, nearest to RHS 148C, and becoming darker towards the margins, nearest to RHS 147B.

Inflorescence: To date, 'PREESMANPT2' has not flowered.

Comparisons with the parent plants: Plants of the new cultivar 'PREESMANPT2' differ from the parent, *Primulina dryas* 'Preesman PT' (Dutch Plant Breeders' Rights grant number 44601), in the characteristics described in Table 1 below.

TABLE 1

| Characteristic | 'PREESMANPT2' | 'Preesman PT' |
|---|---|---|
| Foliage shape. | Broadly ovate. | Narrowly ovate. |
| General coloration of the mature foliage. | A mixture of yellow-green and greyed-green, generally appearing as a dark green coloration. | A mixture of yellow-green and green, generally appearing as a lighter shade of green relative to 'PREESMANPT2'. |
| Expression of leaf color pattern. | Prominent light greyed-green reticulate pattern. | None. |

Plants of the new cultivar 'PREESMANPT2' differ from the most similar commercial variety known to the inventor,

*Primulina dryas* 'Latifolia Dwarf' (not patented), in the characteristics described in Table 2 below.

TABLE 2

| Characteristic | 'PREESMANPT2' | 'Latifolia Dwarf' |
|---|---|---|
| Foliage aspect. | Substantially more concaved, relative to 'Latifolia Dwarf'. | Much less concaved, relative to 'PREESMANPT2'. |
| General coloration of the mature foliage. | A mixture of yellow-green and green; generally appearing as a lighter shade of green relative to 'Latifolia Dwarf'. | A mixture of yellow-green and green; generally appearing as a darker shade of green relative to 'PREESMANPT2'. |

TABLE 2-continued

| Characteristic | 'PREESMANPT2' | 'Latifolia Dwarf' |
|---|---|---|
| Expression of leaf color pattern. | Prominent light greyed-green reticulate pattern; more prominent than 'Latifolia Dwarf'. | Prominent light greyed-green reticulate pattern, yet less prominent than 'PREESMANPT2'. |

That which is claimed is:

1. A new and distinct variety of *Primulina dryas* plant named 'PREESMANPT2', substantially as described and illustrated herein.

* * * * *